US010765614B2

(12) United States Patent
Behler et al.

(10) Patent No.: US 10,765,614 B2
(45) Date of Patent: Sep. 8, 2020

(54) AQUEOUS SURFACTANT COMPOSITIONS

(71) Applicant: BASF SE, Ludwigshafen am Rhein (DE)

(72) Inventors: Ansgar Behler, Düsseldorf-Holthausen (DE); Frank Clasen, Düsseldorf-Holthausen (DE); Claudia Brunn, Düsseldorf-Holthausen (DE); Laurence Pottie, Cologne (DE); Monika Barbenheim, Düsseldorf-Holthausen (DE); Daniel Hoff, Düsseldorf-Holthausen (DE)

(73) Assignee: BASF SE, Ludwigshafen (DE)

( * ) Notice: Subject to any disclaimer, the term of this patent is extended or adjusted under 35 U.S.C. 154(b) by 16 days.

(21) Appl. No.: 16/071,957

(22) PCT Filed: Jan. 19, 2017

(86) PCT No.: PCT/EP2017/051110
§ 371 (c)(1),
(2) Date: Jul. 23, 2018

(87) PCT Pub. No.: WO2017/129470
PCT Pub. Date: Aug. 3, 2017

(65) Prior Publication Data
US 2019/0021972 A1    Jan. 24, 2019

(30) Foreign Application Priority Data
Jan. 29, 2016 (EP) ..................................... 16153359

(51) Int. Cl.
| A61K 8/46 | (2006.01) |
| A61K 8/24 | (2006.01) |
| A61K 8/365 | (2006.01) |
| A61Q 5/02 | (2006.01) |
| A61Q 11/00 | (2006.01) |
| A61Q 19/10 | (2006.01) |
| C11D 3/04 | (2006.01) |
| C11D 3/20 | (2006.01) |
| C11D 1/28 | (2006.01) |
| A61Q 9/02 | (2006.01) |
| C11D 1/12 | (2006.01) |
| C11D 3/06 | (2006.01) |
| C11D 11/00 | (2006.01) |

(52) U.S. Cl.
CPC ............ *A61K 8/463* (2013.01); *A61K 8/24* (2013.01); *A61K 8/365* (2013.01); *A61Q 5/02* (2013.01); *A61Q 9/02* (2013.01); *A61Q 11/00* (2013.01); *A61Q 19/10* (2013.01); *C11D 1/123* (2013.01); *C11D 1/28* (2013.01); *C11D 3/042* (2013.01); *C11D 3/06* (2013.01); *C11D 3/2086* (2013.01); *C11D 11/0023* (2013.01); *A61K 2800/52* (2013.01)

(58) Field of Classification Search
None
See application file for complete search history.

(56) References Cited

U.S. PATENT DOCUMENTS

| 5,366,665 A | 11/1994 | Cho | |
| 9,790,172 B2 * | 10/2017 | Behler | ...................... C11D 1/28 |
| 2006/0258544 A1 * | 11/2006 | Saini | ...................... C09K 8/035 |
| | | | 507/219 |
| 2016/0102050 A1 | 4/2016 | Behler et al. | |

FOREIGN PATENT DOCUMENTS

| DE | 4003096 A1 | 8/1991 |
| DE | 4340042 A1 | 6/1995 |
| EP | 0 530 866 A1 | 3/1993 |
| EP | 2 810 935 A1 | 12/2014 |
| WO | WO-2012/113829 A1 | 8/2012 |
| WO | WO2014195210 | * 12/2014 |

OTHER PUBLICATIONS

McIlvaine J. Biol. Chem. vol. 49, p. 183-186 (Year: 1921).*
International Search Report for Patent Application No. PCT/EP2017/051110, dated Mar. 6, 2017.

* cited by examiner

*Primary Examiner* — Katherine Peebles
(74) *Attorney, Agent, or Firm* — Marshall, Gerstein & Borun LLP

(57) ABSTRACT

Compositions containing
one or more alkyl lactate sulfate (A) of the general formula (I), $$R^1(OCOCH(CH_3))_nOSO_3M^1 \quad (I)$$

in which the radical $R^1$ is a linear or branched alkyl or alkenyl radical having 6 to 30 carbon atoms, the index n is a number in the range from 1 to 5, and the radical $M^1$ is selected from H, Li, Na, K, Ca/2, Mg/2, ammonium, and alkanolamine,
one or more compound (B) selected from phosphoric acid and the mono-, di- and tri-salts thereof, wherein the cation of these salts is selected from Li, Na, K, Ca, Mg, ammonium, and alkanolamine,
one or more compound (C) selected from citric acid and the mono-, di- and tri-salts thereof, wherein the cation of these salts is selected from Li, Na, K, Ca, Mg, ammonium, and alkanolamine, and
water
where the following provisos apply:
the weight ratio of the sum total of the compounds (B) and (C) to the sum total of the compound (A) is in the range from 1:5 to 1:10.
the weight ratio of the sum total of the compound (B) to the sum total of the compound (C) is in the range from 1:1.2 to 1:3.
the pH of the compositions is in the range from 4.5 to 7.5.

13 Claims, No Drawings

AQUEOUS SURFACTANT COMPOSITIONS

CROSS-REFERENCE TO RELATED APPLICATIONS

This is the U.S. national phase of International Application No. PCT/EP2017/051110, filed Jan. 19, 2017, which claims the benefit of European Patent Application No. 16153359.1, filed on Jan. 29, 2016.

FIELD OF THE INVENTION

The present invention relates to storage-stable aqueous compositions having a content of one or more alkyl lactate sulfates.

PRIOR ART

Anionic surfactants are some of the most widespread interface-active compounds and, apart from being used in detergents and cleaners, are also used for diverse purposes in the field of cosmetics. Customary anionic surfactants, as are used especially in cosmetics, are the salts of alkyl ether sulfates (alkyl polyether sulfates, fatty alcohol polyglycol ether sulfates, in short also referred to as ether sulfates). They are characterized by a strong foaming ability, high cleaning power, low sensitivity to hardness and grease and are used widely for producing cosmetic products such as, for example, hair shampoos, foam or shower baths, but also in hand dishwashing detergents.

DE 40,03,096 A1 describes sulfated hydroxycarboxylic esters and use thereof as surface-active substances.

EP 2,810,935 A1 describes sulfated esters of oligohydroxycarboxylic acids and use thereof as surface-active substances.

DESCRIPTION OF THE INVENTION

EP 2,810,935 A1 mentioned above describes sulfated esters of oligohydroxycarboxylic acids as surface-active substances (surfactants), wherein these compounds exhibit a certain tendency to hydrolysis due to the ester groups, which has a negative impact on the storage stability. The object of the present invention consists of providing aqueous surfactant compositions comprising the compounds of the type described in EP 2,810,935 A1 by means of the formula (I) specified therein, in which the radical $R^3$ denotes a methyl group and wherein the index n, in addition to the definition specified therein, can also be zero, and which for practical purposes have sufficient storage stability.

In the context of the present application, storage stability is understood to mean that the pH of the compositions according to the invention at 90 days' storage at 40° C. changes downwardly, i.e. toward a lower pH, by 1.2 or less. Example: At a starting pH of 5.9, the pH of the composition at 90 days' storage at 40° C. lowers at most to 4.7.

The invention additionally provides compositions comprising one or more alkyl lactate sulfates (A) of the general formula (I), $$R^1(OCOCH(CH_3))_n OSO_3 M^1 \qquad (I)$$

in which the radical $R^1$ is a linear or branched alkyl or alkenyl radical having 6 to 30 carbon atoms, the index n is a number in the range from 1 to 5, and the radical $M^1$ is selected from the group comprising H, Li, Na, K, Ca/2, Mg/2, ammonium and alkanolamine, one or more compounds (B) selected from the group comprising phosphoric acid and the mono-, di- and tri-salts thereof, wherein the cation of these salts is selected from the group comprising Li, Na, K, Ca, Mg, ammonium and alkanolamine, one or more compounds (C) selected from the group comprising citric acid and the mono-, di- and tri-salts thereof, wherein the cation of these salts is selected from the group comprising Li, Na, K, Ca, Mg, ammonium and alkanolamine, and water, where the following provisos apply:

the weight ratio of the sum total of the compounds (B) and (C) to the compounds (A) is in the range from 1:5 to 1:10;

the weight ratio of the sum total of the compounds (B) to the sum total of the compounds (C) is in the range from 1:1.2 to 1:3; and the pH of the compositions is in the range from 4.5 to 7.5.

The Compounds (A)

The compounds (A), which are referred to here as alkyl lactate sulfates, are obligatory for the aqueous surfactant compositions according to the invention. They have the formula (I) specified above $$R^1(OCOCH(CH_3))_n OSO_3 M^1 \qquad (I)$$

in which the radical $R^1$ is a linear or branched alkyl or alkenyl radical having 6 to 30 carbon atoms, the index n is a number in the range from 1 to 5, and the radical $M^1$ is selected from the group comprising H, Li, Na, K, Ca/2, Mg/2, ammonium and alkanolamine.

It is expressly stated that the designation of the compounds (A) as alkyl lactate sulfates serves merely for a linguistically simple designation of the compounds (A) and should not be understood as being structurally limiting; hence in the definition according to the formula of the compounds (A) it is clarified that the radical $R^1$ can mean either an alkyl or an alkenyl radical and also—as the index n shows—that they can be alkyl or alkenyl lactate sulfates or alkyl or alkenyl oligolactate sulfates.

The index number n in the general formula (I) specifies the degree of oligomerization. The degree of oligomerization of the compounds (I) is between 1 and 5 and preferably between 1.05 and 2.0. Whereas n in an individual molecule of the formula (I) must always be an integer and here in particular assumes the values in the range from 1 to 5, the value n for an alkyl lactate sulfate which is a mixture of different molecules (I), which differ in their respective individual n values, is an analytically determined calculated parameter which in most cases is a fraction. Preferably, alkyl oligolactate sulfates are used having an average degree of oligomerization n in the range from 1.1 to 1.5.

The radical $R^1$ is preferably derived from saturated, linear, primary alcohols having 10 to 18 carbon atoms and preferably 12 to 16 carbon atoms and especially 12 to 14 carbon atoms. Typical examples of suitable radicals $R^1$ are octyl, decyl, undecyl, dodecyl and myristyl. They are derived from the saturated fatty alcohols caprylic alcohol (octanol-1), capric alcohol (decanol-1), undecanol-1, lauryl alcohol (dodecanol-1) and myristyl alcohol (tetradecanol-1), as are obtained for example in the hydrogenation of technical-grade fatty acid methyl esters or in the course of the hydrogenation of aldehydes during Roelen oxo synthesis.

The radical $M^1$ of the compounds (I) is selected, as listed above, from the group comprising H, Li, Na, K, Ca/2, Mg/2, ammonium and alkanolamine. In this connection, particularly preferred alkanolamines are monoethanolamine, diethanolamine, triethanolamine and monoisopropanolamine.

In a particularly preferred embodiment of the compounds (I), the radical $M^1$ signifies sodium (Na) and/or potassium (K).

The compounds (A) can be prepared by all methods known appropriately to the person skilled in the art. A particularly preferred method for the preparation in this case is the reaction of alcohols $R^1OH$, in which $R^1$ has the definition specified above, with the corresponding amount of lactic acid $CH_3$—$CH(OH)$—$COOH$, which corresponds to the name 2-hydroxypropanoic acid in IUPAC nomenclature, together with subsequent sulfation with gaseous sulfur trioxide and, if desired, neutralization of the acidic sulfation products.

In a preferred embodiment, the radical $R^1$ in the compounds (A) denotes a linear, saturated alkyl radical having 10 to 18 carbon atoms.

The radical $R^1$ in the compounds (A) preferably denotes a linear, saturated alkyl radical having 12 to 16 carbon atoms, wherein especially mixtures of compounds (A) are preferred in which the radical $R^1$ is a lauryl radical to an extent of about 70% by weight and is a myristyl radical to an extent of about 30% by weight.

The Compounds (B)

The compounds (B) are selected from the group comprising phosphoric acid and the mono-, di- and tri-salts thereof, wherein the cation of these salts is selected from the group comprising Li, Na, K, Ca, Mg, ammonium and alkanolamine. In this connection, particularly preferred alkanolamines are monoethanolamine, diethanolamine, triethanolamine and monoisopropanolamine. In a particularly preferred embodiment of the compounds (B), the cation is sodium (Na) and/or potassium (K).

In general, depending on the pH of the compositions—and in this context it is expressly noted that the pH of the aqueous compositions according to the invention is an obligatory parameter—mixtures of different substances (B) are present.

The Compounds (C)

The compounds (C) are selected from the group comprising citric acid and the mono-, di- and tri-salts thereof, wherein the cation of these salts is selected from the group comprising Li, Na, K, Ca, Mg, ammonium and alkanolamine. In this connection, particularly preferred alkanolamines are monoethanolamine, diethanolamine, triethanolamine and monoisopropanolamine. In a particularly preferred embodiment of the compounds (C), the cation is sodium (Na) and/or potassium (K).

In general, depending on the pH of the compositions—and in this context it is expressly noted that the pH of the aqueous compositions according to the invention is an obligatory parameter —mixtures of different substances (C) are present.

Preferred Embodiments

As explained above, the following provisos apply to the compositions according to the invention:
the weight ratio of the sum total of the compounds (B) and (C) to the sum total of the compounds (A) is in the range from 1:5 to 1:10, and preferably in the range from 1:6 to 1:7.5.
the weight ratio of the sum total of the compounds (B) to the sum total of the compounds (C) is in the range from 1:1.2 to 1:3, and preferably in the range from 1:1.5 and 1:2.5.
the pH of the compositions is in the range from 4.5 to 7.5 and preferably in the range from 5.0 to 7.0 and especially in the range from 5.7 to 6.7.

Optional Embodiments

In one embodiment, the aqueous surfactant compositions according to the invention comprise, in addition to the compounds (A), (B), (C) and water, additionally one or more alcohols (D), alkyl sulfates (E), alkyl lactates (F), lactic acid (G), lactic acid sulfate (H), sulfuric acid salts (H) and inorganic salts (S). In this case, the proviso applies that the sum total of all compounds (D) to (S) —specified as % by weight, based on the overall composition—is less than the amount of the compounds (A)—likewise specified as % by weight, based on the overall composition. In a preferred embodiment, the amount of the compounds (A) is in this case 5 to 50% by weight, based on the overall composition—and especially 8 to 40% by weight.

These compounds (D) to (H) are described below:

The Compounds (D)

The compounds (D) are alcohols of the formula $R^1$—OH, where $R^1$ is as defined above for the compounds (A).

The Compounds (E)

The compounds (E) are alkyl sulfates of the formula $R^1$—$OSO_3M^1$, where $R^1$ and $M^1$ are as defined above for the compounds (A).

The Compounds (F)

The compounds (F) are alkyl lactates of the formula $R^1(OCOCH(CH_3))_nOH$ where $R^1$ and n are as defined above for the compounds (A).

The Compounds (G)

The compounds (G) are lactic acid (2-hydroxypropanoic acid), which corresponds to the well-known formula $HOCOCH(CH_3)OH$.

The Compounds (H)

The compounds (H) are lactic acid sulfate, which corresponds to the formula $HOCOCH(CH_3)OSO_3M^1$, where $M^1$ is as defined above for the compounds (A).

The Compounds (S)

The compounds (S) are inorganic salts of sulfuric acid. These salts have the formula $(M^1)_2SO_4$, where $M^1$ is as defined above for the compounds (A).

If desired, the aqueous surfactant compositions according to the invention can additionally comprise one or more further surfactants which, in structural terms, do not belong to the aforementioned compounds (A) and (E). These surfactants may be anionic, cationic, nonionic or amphoteric surfactants.

Use of the Compositions

A further subject matter of the invention is the use of the aforementioned compositions for cosmetic products, and also detergents and cleaners.

With regard to cosmetic products, particular preference is given here especially to those which are present in the form of hair shampoos, shower gels, soaps, syndets, washing pastes, washing lotions, scrub preparations, foam baths, oil baths, shower baths, shaving foams, shaving lotions, shaving creams and dental care products (for example toothpastes, mouthwashes and the like).

EXAMPLES

Substances Used

CD water=completely demineralized water
Alkyl lactate sulfate ALS-I: Aqueous composition comprising a compound (A), where the following parameters apply: n=1.11 (average of the species where n=1 and n=2); $R^1$=70% $C_{12}$ and 30% $C_{14}$; $M^1$=Na, also the compounds (D) to (S). Analysis: The composition comprises 9.4% by weight (A) and in total 6.3% by weight of the compounds (D) to (S), remainder water. At 20° C., the composition is a clear, homogeneous pale yellow liquid.

Alkyl lactate sulfate ALS-II: Aqueous composition comprising a compound (A), where the following parameters apply: n=1.23 (average of the species where n=1 and n=2); $R^1$=70% $C_{12}$ and 30% $C_{14}$; $M^1$=Na, also the compounds (D) to (S). Analysis: The composition comprises 10.9% by weight (A) and in total 4.6% by weight of the compounds (D) to (S), remainder water. At 20° C., the composition is a clear, homogeneous pale yellow liquid.

Potassium dihydrogenphosphate: $KH_2PO_4$, ≥99% p.a. (chemical trade)

Sodium citrate: Trisodium citrate dihydrate, ≥99% p.a. (chemical trade)

Measurement and Test Methods pH: Using a standard commercial pH meter, the pH was measured directly in the formulation, i.e. the aqueous surfactant composition.

Active substance content: The anionic surfactant content was determined by Epton titration (in accordance with ISO 2271), this being acquired for the content of the compounds (A) and (E).

Appearance: The samples to be tested were stored in 250 ml glass bottles and assessed visually with respect to the emergence of cloudiness, inhomogeneity (e.g. precipitations, streaks, sedimentation) and especially phase separation since this is an indicator of hydrolysis. In the case of the samples used, the fatty alcohol released by hydrolysis floated upward.

Storage test: The samples were stored in 250 ml glass bottles in a drying cabinet at 40° C. and taken at regular intervals, cooled to 20° C. and the appearance then assessed. If the solutions were still monophasic, clear and homogeneous, the pH was measured and the samples returned to the drying cabinet.

In the case of storage of the sample according to Example B2, the anionic surfactant content was also determined monthly in order to monitor the pH decrease and to correlate appearance of the sample with degradation of the anionic surfactant content.

Example B1

To the alkyl lactate sulfate ALS-I were added 0.5% potassium dihydrogenphosphate and 1.0% sodium citrate—% by weight respectively based on the overall composition—and the mixture was then stirred at 20° C. until all solids had dissolved and a clear homogeneous solution was present. The starting pH of the solution was measured. The sample was subsequently stored as described above. The measurement data are found in Tables 1 and 2.

Comparative Example CE1

Analogous to Example B1 but without addition of buffer substances. The measurement data are found in Tables 1 and 2.

Comparative Examples CE2 to CE4

Analogous to Example B1 but with varying amounts of potassium dihydrogenphosphate and sodium citrate. The measurement data are found in Tables 1 and 2.

TABLE 1

Overview of Examples/Comparative examples

|      | Starting pH | $KH_2PO_4$ | Sodium citrate |
|------|-------------|------------|----------------|
| CE 1 | 6.7         | 0 wt %     | 0 wt %         |
| CE 2 | 6.2         | 0.5 wt %   | 0 wt %         |
| CE 3 | 6.1         | 0 wt %     | 0.5 wt %       |
| CE 4 | 5.7         | 0.5 wt %   | 0.5 wt %       |
| B 1  | 5.9         | 0.5 wt %   | 1.0 wt %       |

TABLE 2 pH change (starting pH minus pH of the sample after x days) during storage at 40° C.

|      | 7 days | 13 days | 20 days | 28 days | 41 days | 62 days | 81 days | 90 days | 125 days | 178 days |
|------|--------|---------|---------|---------|---------|---------|---------|---------|----------|----------|
| CE 1 | −1.9   |         | −2.7    | X       |         |         |         |         |          |          |
| CE 2 | −0.3   | −0.7    | −0.7    | −0.8    | −1.0    | −2.3    | X       |         |          |          |
| CE 3 | −0.6   | −0.9    | −0.9    | −1.0    | −1.1    | −1.6    | −2.3    | X       |          |          |
| CE 4 | −0.3   | −0.7    | −0.6    | −0.7    | −0.8    | −1.3    | −2.0    | X       |          |          |
| B 1  | −0.2   | −0.6    | −0.5    | −0.5    | −0.5    | −0.8    | −1.0    | −1.1    | −1.3     | X        |

X = sample was biphasic

According to Table 2, the sample B1 on storage at 40° C. remained homogeneous and clear the longest and showed the lowest pH decrease and thus the best stability to hydrolysis.

The storage stability was distinctly improved compared to the unbuffered sample (comparative example CE1).

The buffer substances alone (comparative examples CE2 and CE3) or combined in a different ratio (comparative example CE4) showed a significantly worse result than B1.

Example B2

To the alkyl lactate sulfate ALS-II were added 0.5% potassium dihydrogenphosphate and 1.0% sodium citrate and the mixture was then stirred at 20° C. until all solids had dissolved and a clear homogeneous solution was present. Anionic surfactant content, pH and appearance of the samples during storage were determined. It is apparent from Table 3 that the decrease of the pH and the appearance of the sample correlate with a decrease in the anionic surfactant content.

TABLE 3

Anionic surfactant content, pH and appearance of the example sample B2 during storage at 40° C.

| | Start | 1 month | 2 months | 3 months | 4 months | 5 months | 6 months | 7 months |
|---|---|---|---|---|---|---|---|---|
| Anionic surfactant [% by wt] | 14.7 | 14.3 | 13.9 | 13.5 | 13.3 | 12.9 | 12.5 | 11.7 |
| pH | 6.70 | 6.14 | 5.97 | 5.89 | 5.34 | 5.06 | 4.70 | 4.31 |
| Appearance | clear | clear | clear | clear | clear | slight streaks, clear again after shaking | milky cloudy | biphasic |

The invention claimed is:

1. A composition comprising:
one or more alkyl lactate sulfate (A) of the general formula (I), $$R^1(OCOCH(CH_3))_nOSO_3M^1 \quad (I)$$

in which the radical $R^1$ is a linear or branched alkyl or alkenyl radical having 6 to 30 carbon atoms, the index n is a number in the range from 1 to 5, and the radical $M^1$ is selected from the group consisting of H, Li, Na, K, Ca/2, Mg/2, ammonium, and alkanolamine,
   one or more compound (B) selected from the group consisting of phosphoric acid and the mono-, di- and tri-salts thereof, wherein a cation of these salts is selected from the group consisting of Li, Na, K, Ca, Mg, ammonium, and alkanolamine,
   one or more compound (C) selected from the group consisting of citric acid and the mono-, di- and tri-salts thereof, wherein a cation of these salts is selected from the group consisting of Li, Na, K, Ca, Mg, ammonium, and alkanolamine, and
   water;
where the following provisos apply:
   the weight ratio of the sum total of the compounds (B) and (C) to the sum total of the compound (A) is in a range from 1:5 to 1:10;
   the weight ratio of the sum total of the compound (B) to the sum total of the compound (C) is in a range from 1:1.2 to 1:3; and
   the pH of the composition is in the range from 4.5 to 7.5.

2. The composition according to claim 1, wherein the radical $R^1$ in the formula (I) is a saturated linear alkyl radical having 12 to 16 carbon atoms.

3. The composition according to claim 1, wherein the radical $M^1$ is sodium (Na) or potassium (K).

4. The composition according to claim 1, wherein the one or more compound (A) is present in a range from 5% to 50% by weight—based on the overall composition.

5. The composition according to claim 1, wherein the pH of the composition is in the range from 5.0 to 7.

6. The composition according to claim 1, wherein the weight ratio of the sum total of compounds (B) and (C) to the compound (A) is in the range from 1:6 to 1:7.5.

7. The composition according to claim 1, wherein the weight ratio of the compound (B) to the compound (C) is in the range from 1:1.5 to 1:2.5.

8. The composition according to claim 1 for use in cosmetic products, detergents, and cleaners.

9. The composition according to claim 1 for use in cosmetic products in the form of hair shampoos, shower gels, soaps, syndets, washing pastes, washing lotions, scrub preparations, foam baths, oil baths, shower baths, shaving foams, shaving lotions, shaving creams, and dental care products.

10. The composition according to claim 1 for use in products for cleaning hard surfaces.

11. The composition according to claim 10 wherein the product is a bath cleaner or a toilet cleaner.

12. The composition according to claim 1 for use in a fragrance gel.

13. The compostion according to claim 1, wherein:
   the pH of the composition is in the range from 5.0 to 7;
   the weight ratio of the sum total of compounds (B) and (C) to the compound (A) is in the range from 1:6 to 1:7.5; and
   the weight ratio of the compound (B) to the compound (C) is in the range from 1:1.5 to 1:2.5.

* * * * *